United States Patent
Constantz

(12) 
(10) Patent No.: US 6,375,935 B1
(45) Date of Patent: Apr. 23, 2002

(54) CALCIUM PHOSPHATE CEMENTS PREPARED FROM SILICATE SOLUTIONS

(76) Inventor: Brent R. Constantz, 191 Jefferson, Menlo Park, CA (US) 94025

( * ) Notice: Subject to any disclaimer, the term of this patent is extended or adjusted under 35 U.S.C. 154(b) by 0 days.

(21) Appl. No.: 09/561,324

(22) Filed: Apr. 28, 2000

(51) Int. Cl.⁷ .............................. A61K 7/16; A61K 9/14; A61F 2/00
(52) U.S. Cl. ..................... 424/57; 424/400; 424/423; 424/484; 424/489; 424/49
(58) Field of Search ................................. 424/400, 401, 424/489, 422, 423; 514/951, 953

(56) References Cited

U.S. PATENT DOCUMENTS

| | | |
|---|---|---|
| 4,160,012 A | 7/1979 | Ono et al. |
| 4,161,511 A | 7/1979 | Shiraki et al. |
| 4,165,368 A * | 8/1979 | Gaffar ..................... 424/52 |
| 4,429,691 A | 2/1984 | Niwa et al. |
| 4,497,075 A | 2/1985 | Niwa et al. |
| 4,990,163 A | 2/1991 | Ducheyne et al. |
| 5,281,265 A | 1/1994 | Liu |
| 5,525,148 A | 6/1996 | Chow et al. |
| 5,545,254 A | 8/1996 | Chow et al. |
| 5,580,623 A | 12/1996 | Fulmer et al. |
| 5,679,294 A | 10/1997 | Umezu et al. |
| 5,695,729 A | 12/1997 | Chow et al. |
| 5,697,981 A | 12/1997 | Ison et al. |
| 5,900,254 A | 5/1999 | Constantz |
| 5,954,867 A | 9/1999 | Chow et al. |
| 5,962,028 A | 10/1999 | Constantz |
| 5,968,253 A | 10/1999 | Poser et al. |
| 5,976,234 A | 11/1999 | Chow et al. |
| 5,997,624 A | 12/1999 | Chow et al. |
| 6,005,162 A | 12/1999 | Constantz |
| 6,027,742 A | 2/2000 | Lee et al. |

OTHER PUBLICATIONS (1999). "Production and characterization of new calcium phosphate cements in the CAHPO4–alpha–CA3(PO4)2 system: pH, workability, and setting times" *J. Materials Science: Materials in Medicine*, vol. 10:223–230.

* cited by examiner

Primary Examiner—Thurman K. Page
Assistant Examiner—Charesse L. Evans
(74) Attorney, Agent, or Firm—Bret E. Field; Bozicevic, Field & Francis

(57) ABSTRACT

Methods are provide for producing flowable compositions, e.g. pastes, that set into calcium phosphate products. In the subject methods, dry reactants that include a calcium source and a phosphate source are combined with a solution of a soluble silicate, e.g. sodium silicate, and the combined liquids and solids are mixed to produce the flowable composition. Also provided are the compositions themselves as well as kits for preparing the same. The subject methods and compositions produced thereby find use in a variety of applications, including the repair of hard tissue defects, e.g. bone defects.

35 Claims, No Drawings

CALCIUM PHOSPHATE CEMENTS PREPARED FROM SILICATE SOLUTIONS

FIELD OF THE INVENTION

The field of this invention is calcium phosphate cements.

BACKGROUND

Calcium phosphate cements which are prepared by combining a dry component(s) and a liquid to form a flowable paste like material that is subsequently capable of setting into a solid calcium phosphate product hold great promise for use as structural materials in the orthopedic and dental fields. For example, it is desirable to be able to inject a flowable material into a cancellous bone void and have the material set into a solid calcium phosphate mineral product that is capable of withstanding physiological loads. Materials that set into solid calcium phosphate mineral products are of particular interest as such products can closely resemble the mineral phase of natural bone and are susceptible to remodeling, making such products extremely attractive for use in orthopedics and related fields.

While a large number of different calcium phosphate cement formulations have been developed, there is a continued need for the development of yet more advanced formulations. Of particular interest is the development of formulations that set in a clinically relevant period of time into products that have sufficient strength to serve as cancellous and cortical bone substitutes and are capable of being replaced over time with natural bone.

Relevant Literature

Calcium phosphate compositions relevant to this invention include, but are not limited to those described in: "Production and Characterization of New Calcium Phosphate Cements in the CAHPO4-alpha-CA3(PO4)2 System: pH, Workability and Setting Times"; J. Materials Science: Materials in Medicine, v. 10 (1999) pp.223–230. Representative Patents describing calcium phosphate cements include: U.S. Pat. Nos. 6,027,742; 6,005,162; 5,997,624; 5,976,234; 5,968,253; 5,962,028; 5,954,867; 5,900,254; 5,697,981; 5,695,729; 5,679,294; 5,580,623; 5,545,254; 5,525,148; 5,281,265; 4,990,163; 4,497,075; and 4,429,691. Sodium hexafluorosilicate is described in U.S. Pat. Nos.: 4,161,511 and 4,160,012.

SUMMARY OF THE INVENTION

Methods are provided for producing flowable compositions, e.g. injectable pastes, that set into calcium phosphate products. In the subject methods, dry reactants that include a calcium source and a phosphate source are combined with a solution of a soluble silicate, e.g. sodium silicate, and the combined liquids and solids are mixed to produce the flowable composition. Also provided are the compositions themselves as well as kits for preparing the same. The subject methods and compositions produced thereby find use in a variety of applications, including the repair of hard tissue defects, e.g. bone defects.

DESCRIPTION OF THE SPECIFIC EMBODIMENTS

Methods are provided for producing flowable compositions, e.g. injectable pastes, that set into calcium phosphate products. In the subject methods, dry reactants that include a calcium source and a phosphate source are combined with a solution of a soluble silicate, e.g. sodium silicate, and the combined liquids and solids are mixed to produce the flowable composition. Also provided are the compositions themselves as well as kits for preparing the same. The subject methods and compositions produced thereby find use in a variety of applications, including the repair of hard tissue defects, e.g. bone defects. In further describing the subject invention, the subject methods will be described first, followed by a description of the compositions produced thereby, kits for use in preparing the same and methods for using the subject compositions in methods of hard tissue, e.g. bone repair.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

METHODS

In the subject methods, dry reactants that include a calcium source and a phosphate source are combined with a solution of a soluble silicate under conditions sufficient to produce a flowable composition that sets into a calcium phosphate containing product, even when immersed.

A feature of the subject methods is that a solution of a soluble silicate is employed. By solution of a soluble silicate is meant an aqueous solution in which a silicate compound is dissolved and/or suspended. The silicate compound may be any compound that is physiologically compatible and is soluble in water. By soluble in water is meant a concentration of at least about 1%, usually at least about 2% and more usually at least about 5%, where the concentration of the silicate employed typically ranges from about 0 to 20%, usually from about 5 to 15% and more usually from about 5 to 10%. Representative silicates of interest include, but are not limited to: sodium silicates, potassium silicates, borosilicates, magnesium silicates, aluminum silicates, zirconium silicates, potassium aluminum silicates, magnesium aluminum silicates, sodium aluminum silicates, sodium methylsilicates, potassium methylsilicates, sodium butylsilicates, sodium propylsilicates, lithium propylsilicates, triethanol ammonium silicates, tramethanolamine silicates, zinc hexafluorosilicate, ammonium hexafluorosilicate, cobalt hexafluorosilicate, iron hexafluorosilicate, potassium hexafluorosilicate, nickel hexafluorosilicate, barium hexafluorosilicate, hydroxyammonium hexafluorosilicate, sodium hexafluorosilicate and calcium fluorosilicate. The preparation of sodium hexafluorosilicate is described in U.S. Pat. Nos. 4,161,511 and 4,160,012; the disclosures of which are herein incorporated by reference. Of particular interest in many embodiments are solutions of sodium silicate, where the manufacture of dry sodium silicate ($Na_2SiO_3$, $Na_6Si_2O_7$ and $Na_2Si_3O_7$) is described in Faith, Keyes & Clark's INDUSTRIAL CHEMICALS (1975) pp 755–761.

In the subject methods, the above described soluble silicate solutions are combined with dry reactants that include a calcium source and a phosphate source under conditions sufficient to produce a flowable composition. The dry reactants that are combined with the solution are typically particulate compositions, e.g. powders, where the particle size of the components of the particulate compositions typically ranges from about 1 to 1000 microns, usually from about 1 to 200 um and more usually from about 1 to 40 microns.

As mentioned above, the dry reactants include a calcium source and a phosphate source. The calcium source and phosphate source may be present as a single compound or present as two or more compounds. As such, a single calcium phosphate present in the dry reactants may be the calcium source and the phosphate source. Alternatively, two or more compounds may be present in the dry reactants, where the compounds may be compounds that include calcium, phosphate or calcium and phosphate. Calcium phosphate sources of interest that may be present in the dry reactants include: MCPM (monocalcium phosphate monohydrate or $Ca(H_2PO_4)_2.H_2O$); DCPD (dicalcium phosphate dihydrate, brushite or $CaHPO_4.2H_2O$), ACP (amorphous calcium phosphate or $Ca_3(PO_4)_2H_2O$), DCP (dicalcium phosphate, monetite or $CaHPO_4$), tricalcium phosphate, including both α- and β-$(Ca_3(PO_4)_2$, tetracalcium phosphate $(Ca_4(PO_4)_2O$, etc. Calcium sources of interest include: calcium carbonate ($CaCO_3$), calcium oxide (CaO), calcium hydroxide ($Ca(OH)2$ and the like. Phosphate sources of interest include: Phosphoric acid ($H3PO4$), all soluble phosphates, and the like.

The ratios or relative amounts of each of the disparate calcium and/or phosphate compounds in the dry reactant mixture is one that provides for the desired calcium phosphate product upon combination with the soluble silicate and subsequent setting. In many embodiments, the overall ratio (i.e. of all of the disparate calcium and/or phosphate compounds in the dry reactants) of calcium to phosphate in the dry reactants ranges from about 4:1 to 0.5:1, usually from about 2:1 to 1:1 and more usually from about 1.33:1 to 1.9:1. A variety of calcium phosphate cement compositions are known to those of skill in the art, and such cements may be readily modified into cements of the subject invention by substituting a silicate containing solution for the setting solution of those cements. Cement compositions known to those of skill in the art and of interest include, but are not limited to, those described in U.S. Pat. Nos.: 6,027,742; 6,005,162; 5,997,624; 5,976,234; 5,968,253; 5,962,028; 5,954,867; 5,900,254; 5,697,981; 5,695,729; 5,679,294; 5,580,623; 5,545,254; 5,525,148; 5,281,265; 4,990,163; 4,497,075; and 4,429,691; the disclosures of which are herein incorporated by reference.

One or both of the above liquid and dry reactant components may include an active agent that modulates the properties of the product into which the flowable composition prepared by the subject method sets. Such additional ingredients or agents include: organic polymers, e.g. proteins, including bone associated proteins which impart a number of properties, such as enhancing resorption, angiogenesis, cell entry and proliferation, mineralization, bone formation, growth of osteoclasts and/or osteoblasts, and the like, where specific proteins of interest include osteonectin, bone sialoproteins (Bsp), α-2HS-glycoproteins, bone Gla-protein (Bgp), matrix Gla-protein, bone phosphoglycoprotein, bone phosphoprotein, bone proteoglycan, protolipids, bone morphogenic protein, cartilage induction factor, platelet derived growth factor, skeletal growth factor, and the like; particulate extenders; inorganic water soluble salts, e.g. NaCl, calcium sulfate; sugars, e.g. sucrose, fructose and glucose; pharmaceutically active agents, e.g. antibiotics; and the like In practicing the subject methods, suitable amounts of the dry reactants and the silicate solution are combined to produce a flowable composition. In other words, the ratio of the dry reactants to silicate solution (i.e. the liquid to solids ratio) is selected to provide for a flowable composition. In many embodiments, the liquid to solids ratio is chosen to provide for a flowable composition that has a viscosity ranging from that of milk to that of modeling clay. As such, the liquids to solids ratio employed in the subject methods typically ranges from about 0.2 to 1.0, usually from about 0.3 to 0.6. Of particular interest in many embodiments are methods that produce a paste composition, where the liquid to solids ratio employed in such methods typically ranges form about 0.25 to 0.5, usually from about 0.3 to 0.45. The use of sodium silicate as the liquid allows a lower liquids to solids ratio to be employed which results in a less porous and stronger final hardened mass.

As mentioned above, the requisite amounts of dry reactants and silicate solution are combined under conditions sufficient to produce the flowable product composition. As such, the dry and liquid components are typically combined under agitation or mixing conditions, such that a homogenous composition is produced from the dry and liquid components. Mixing may be accomplished using any convenient means, including manual mixing as described in U.S. Pat. No. 6,005,162 and automated mixing as described in WO 98/28068, the disclosures of which are herein incorporated by reference. Also of interest is the device disclosed in U.S. Pat. No. 5,980,482, the disclosure of which is herein incorporated by reference.

Because the silicate solution enhances the speed and mixablility of the components, a simple cylindrical tube may be used both as a storage and packaging device and a mixing and delivery device. The plastic tube is separated into at least two, and usually two sections, compartments or portions. One section or portion contains the silicate solution, as described above, and another section, compartment or portion contains the powder component, as described above. The two compartments are separated from each other by an easily removable barrier which can be readily removed during preparation of the packaged cement. Any convenient removable barrier may be present in the device, where a representative barrier means of interest is a dialysis bag clips or analogous means. Another representative barrier means of interest is a frangible barrier, as described in WO 98/28068 and U.S. Pat. No. 5,362,654; the disclosures of which are herein incorporated by reference. When one is ready to mix, the clip or other barrier means between the to areas (liquid and powder) is removed (e.g. unclipped), and the contents are simply kneaded together by hand. The above steps may be performed through a second outer covering for sterility—i.e. the above described package elements may be present in a second outer covering for sterility. The outer coving may then be removed and the mixed contents from the tube may be delivered from one end of the storage/mixing tube using a peristaltic action. This mixing device is exceedingly simple to use and inexpensive to supply, with no additional components necessary;—the entire mixing device is disposable. This device provides advantages over that described in U.S. Pat. No. 5,980,482.

The temperature of the environment in which combination or mixing of the dry and liquid components takes place is sufficient to provide for a product that has desired setting and strength characteristics, and typically ranges from about 0 to 50 degrees C, usually from about 20 to 30 degrees C. Mixing takes place for a period of time sufficient for the flowable composition to be produced, and generally takes place for a period of time ranging from about 15 to 100 seconds, usually from about 15 to 50 seconds and more usually from about 15 to 30 second. By employing sodium silicate mixing times are shorter than with other liquids which have been used and the paste has a "slippery" feel.

The above described protocols result in a flowable composition that is capable of setting into a calcium phosphate mineral product, as described in greater detail below.

FLOWABLE COMPOSITIONS

The flowable compositions produced by the above described methods are ones that set into a biologically compatible, and often resorbable and/or remodelable, product. The term flowable is meant to include paste like compositions, as well as more liquid compositions. As such, the viscosity time of the subject flowable compositions, defined as time periods under which the mixed composition injects through a standard Luer-lok fitting after mixing, typically ranges up to 10 minutes, usually up to 7 minutes and more usually up to 4 minutes. Of particular interest in many embodiments are paste compositions that have a injectable viscosity ranging up to 5 minutes, usually from about up to 4 minutes. Pastes that stay paste-like for longer period may be displaced by bleeding bone once inplanted into the body, which create a blood interface between the cement and the bone prior to the cement hardening.

The compositions produced by the subject invention set into calcium phosphate mineral containing products. By calcium phosphate mineral containing product is meant a solid product that includes one or more, usually primarily one, calcium phosphate mineral. In many embodiments, the calcium phosphate mineral is one that is generally poorly crystalline, so as to be resorbable and, often, remodelable, over time when implanted into a physiologically site. The calcium to phosphate ratio in the product may vary depending on particular reactants and amounts thereof employed to product it, but typically ranges from about 2:1 to 1.33:1, usually from about 1.5:1 to 1.8:1 and more usually from about 1:6:1 to 1.7:1. Of particular interest in many embodiments are apatitic products, which apatitic products have a calcium to phosphate ratio ranging from about 1.33:1 to 2.0:1, including both hydroxyapatite and calcium deficient analogs thereof, including carbonate substituted hydroxyapatite (i.e. dahllite), etc. The subject paste-like composition is in many embodiments, preferably one that is capable of setting into a hydroxyapatitic product, and more preferably into a carbonated hydroxyapatite, i. e. dahllite, having a carbonate substitution of from 2 to 10%, usually 2 to 8% by weight of the final product.

The period of time required for the compositions to harden or "set" may vary. By set is meant: the Gilmore Needle Test (ASTM C266-89), modified with the cement submerged under 37 degree C physiological saline. The set times of the subject cements may range from about 30 second to 30 minutes, and will usually range from about 2 to 15 minutes and more usually from about 4 to 12 minutes. In many embodiments, the flowable composition sets in a clinically relevant period of time. By clinically relevant period of time is meant that the paste-like composition sets in less than about 20 minutes, usually less than about 15 minutes and often in less than about 10 minutes, where the composition remains flowable for at least about 1 minute, usually at least about 2 minutes and, in many embodiments, for at least about 5 minutes following combination or mixture of the precursor liquid and dry cement components. The use of silicate solutions cause these cements to set faster than the same cements do when only water is employed; the rate of setting increase positively with increasing silicate concentrations.

The compressive strength of the product into which the flowable composition sets may vary significantly depending on the particular components employed to produce it. Of particular interest in many embodiments is a product that has a compressive strength sufficient for it to serve as at least a cancellous bone structural material. By cancellous bone structural material is meant a material that can be used as a cancellous bone substitute material as it is capable of withstanding the physiological compressive loads experienced by compressive bone under at least normal physiological conditions. As such, the subject flowable paste-like material is one that sets into a product having a compressive strength of at least about 20, usually at least about 40 and more usually at least about 50 MPa, as measured by the assay described in Morgan, EF et al., 1997, Mechanical Properties of Carbonated Apatite Bone Mineral Substitute: Strength, Fracture and Fatigue Behavior. J. Materials Science: Materials in Medicine. V. 8, pp 559–570. where the compressive strength of the final apatitic product may be as high as 60 or higher. Inclusion of the silicate allows lower liquid to solids ratios to be employed which results in significantly higher compressive strengths. Compressive strengths can be obtained that range as high 100 to 200 MPa.

Preferably, the flowable paste like composition is capable of setting in a fluid environment, such as an in vivo environment at a bone repair site. As such, the flowable paste composition can set in a wet environment, e.g. one that is filled with blood and other physiological fluids. Therefore, the site to which the flowable composition is administered during use need not be maintained in a dry state.

APPLICATIONS

The subject methods and compositions produced thereby, as described above, find use in applications where it is desired to introduce a flowable material capable of setting up into a solid calcium phosphate product into a physiological site of interest, such as in dental, craniomaxillofacial and orthopedic applications. In orthopedic applications, the cement will generally be prepared, as described above, and introduced to a bone repair site, such as a bone site comprising cancellous and/or cortical bone. Orthopedic applications in which the cements prepared by the subject system find particular use include the treatment of fractures and/or implant augmentation, in mammalian hosts, particularly humans. In such fracture treatment methodologies, the fracture is first reduced. Following fracture reduction, a flowable structural material prepared by the subject system is introduced into the cancellous tissue in the fracture region using the delivery device described above. Specific dental, craniomaxillofacial and orthopedic indications in which the subject invention finds use include, but are not limited to, those described in WO 98/28068, the disclosure of which is herein incorporated by reference. In yet other embodiments, the subject compositions find use in drug delivery, where they are capable of acting as long lasting drug depots following administration to a physiological site. See e.g. U.S. Pat. Nos. 5,904,718 and 5,968,253; the disclosures of which are herein incorporated by reference.

KITS

Also provided are kits comprising the subject cements, where the dry and liquid components may be present in separate containers in the kit, or some of the components may be combined into one container, such as a kit wherein the dry components are present in a first container and the liquid components are present in a second container, where the containers may or may not be present in a combined configuration, as described in WO 98/28068, the disclosure of which is herein incorporated by reference.

The following examples are offered by way of illustration and not by way of limitation.

EXPERIMENTAL

Example 1

5 grams of Norian SRS combined powder (MCPM, Calcite, alpha-TCP; NSWO#455A) (available from Norian Corporation, Cupertino Calif.) was combined in a glass mortar and pestal with 4.0 grams of sodium silicate liquid (Fischer Scientific). The mixture hardened very rapidly, in less than one minute. There was no apparent or measurable heat evolved. Hardened pieces were immersed in distilled water. The pH of the wetted hard cement was approximately 10.

Example 2

A dilute sodium silicate solution was prepared by dissolving 2 ml of sodium silicate liquid (Fischer Scientific) in 24 ml of distilled water. The pH of this diluted solution was 11.5. 5 grams of Norian SRS combined powder (MCPM, Calcite, alpha-TCP; NSWO#455A) was combined in a glass mortar and pestal with 2.5 grams of the dilute sodium silicate solution. The mixture was ground in a glass mortar and pestal for two minutes, forming a very creamy paste almost instantly. No thermal evolution or odor was observed. At two minutes the paste was 'squeegied' out of the mortar and had a nice, very workable and injectable consistency. The paste was formed into two spheres and immersed in distilled water at room temperature. The spheres were hard to the touch at 10 minutes and it was difficult to make an impression on their surfaces. Distilled water was put in the mortar, exposed to the paste remaining in the mortar which was strongly adherent to the mortar wall and would not wash away with the jet of distilled water. The pH of the water coating the hardened paste was between 7 and 8, approximately 7.8. After immersion in distilled water for one day, one week and one month, the spheres remained intact and appeared to have compressive strength well in excess of 50 mPa.

Example 3

Another preferred base formulation is:
1.5 $CaHPO_4$+0.5 $CaCO_3$+$Ca_3(PO_4)_2$ which is mixed with diluted sodium silicate solution to yield $Ca_5$-⅔$Na_z(PO_4)_3$-⅔x-⅓y$(CO_3)$x$(SiO_4)$yOH+$Na^+$+$HCO_3^-$ (excess)

It is evident from the above results and discussion that calcium phosphate cements employing silicate liquids may be mixed very quickly and easily without specialized mixing devices, set rapidly, and are able to obtain higher strengths due to the lower liquids to solids ratios employed. As such, the subject invention represents a significant contribution to the art.

All publications and patent applications mentioned in this specification are herein incorporated by reference to the same extent as if each individual publication or patent application was specifically and individually indicated to be incorporated by reference.

The invention now being fully described, it will be apparent to one of skill in the art that many changes and modifications can be made thereto without departing from the spirit and scope of the appended claims.

What is claimed is:

1. A method or producing a flowiable composition that sets into a solid calcium phosphate containing product in an in vivo fluid environment, said method comprising:
   combining:
   (a) a silicate solution containing a soluble silicate; and
   (b) dry reactants comprising a calcium source and a phosphate source, wherein said silicate solution and dry reactants are combined in a ratio sufficient to produce a flowable material that sets in an in vivo fluid environment in less than 20 minutes into a solid calcium phosphate containing product having a compressive strength of at least about 20 MPa upon reaction of said calcium and phosphate sources and said soluble silicate.

2. The method according to claim 1, wherein said ratio ranges from about 0.2:1 to 0.7:1.

3. The method according to claim 2, wherein said flowable composition is a paste.

4. The method according to claim 1, wherein said silicate solution is a solution of a soluble silicate having a concentration ranging from about 1% to 15%.

5. The method according to claim 1, wherein said flowable composition sets into said calcium phosphate containing product in a period of time ranging from about 5 to 10 minutes.

6. The method according to claim 1, wherein said calcium phosphate containing product has a compressive strength ranging from about 25 to 100 MPa.

7. A method of producing a paste that sets into a solid calcium phosphate containing product in an in vivo fluid environment, said method comprising:
   (a) combining:
      (i) dry reactants comprising a calcium source and a phosphate source; and
      (ii) a solution of a soluble silicate having a concentration ranging from about 5% to 10%, wherein said dry reactants and said solution are combined in a ratio sufficient to provide for said paste; and
   (b) mixing said combined reactants and solution for a sufficient period of time to produce a paste that sets in an in vivo fluid environment in less than 20 minutes into a solid calcium phosphate containing product having a compressive strength of at least about 20 MPa upon reaction of said calcium and phosphate sources and said soluble silicate.

8. The method according to claim 7, wherein said ratio ranges from about 0.3 to 0.5.

9. The method according to claim 7, wherein said paste sets in a period of time ranging from about 4 to 10 minutes into a calcium phosphate containing product having a compressive strength ranging from about 40 to 70 MPa.

10. The method according to claim 7, wherein said soluble silicate is sodium silicate.

11. A flowable composition that sets into a solid calcium phosphate contain product in an in vivo fluid environment, wherein said composition is produced by the method comprising:
    combining dry reactants comprising a source of calcium and phosphate with a solution of a soluble silicate; and
    mixing said combined dry reactants and solution for a period of time sufficient to produce said flowable product that sets in an in vivo fluid environment in less than 20 minutes into a solid calcium phosphate containing product having a compressive strength of at least about 20 MPa upon reaction of said calcium and phosphate sources and said soluble silicate.

12. The composition according to claim 11, wherein said composition is a paste.

13. The composition according to claim 11, wherein said calcium phosphate containing product is an apatitic product.

14. The composition according to claim 11, wherein said composition sets in period of time ranging from about 4 to 12 minutes.

15. The composition according to claim 11, wherein said calcium phosphate containing product has a compressive strength ranging from about 25 to 100.

16. A kit for use in a preparing a flowable composition that sets in an in vivo fluid environment into a calcium phosphate product, said kit comprising:
 (a) dry reactants comprising a calcium source and a phosphate source that produce a flowable composition upon combination with a solution of a soluble silicate, wherein said flowable composition sets in an in vivo fluid environment in less than 20 minutes into a solid calcium phosphate containing product having a compressive strength of at least about 20 MPa upon reaction of said calcium and phosphate sources; and
 (b) a solution of a soluble silicate.

17. The kit according to claim 16, wherein said soluble silicate has a concentration ranging from about 5 to 10%.

18. The kit according to claim 16, wherein said soluble silicate is a sodium silicate.

19. A method of repairing a hard tissue defect, said method comprising:
 applying to the site of said defect a flowable composition that sets in an in vivo fluid environment into a solid calcium phosphate containing product, wherein said composition is produced by the method comprising:
  (a) combining dry reactants comprising a source of calcium and phosphate with a solution of a soluble silicate; and
  (b) mixing said combined dry reactants and solution for a period of time sufficient to produce said flowable product that sets in an in vivo fluid environment in less than 20 minutes into a solid calcium phosphate containing product having a compressive strength of at least about 20 MPa upon reaction of said calcium and phosphate sources and said soluble silicate.

20. The method according to claim 19, wherein said composition is a paste.

21. The method according to claim 19, wherein said calcium phosphate containing product is an apatitic product.

22. The method according to claim 19, wherein said composition sets in period of time ranging from about 4 to 12 minutes.

23. The method according to claim 19, wherein said calcium phosphate containing product has a compressive strength ranging from about 25 to 100 MPa.

24. The method according to claim 19, wherein said hard tissue is bone.

25. The method according to claim 24, wherein said defect is a reduced fracture.

26. The method according to claim 24, wherein said defect is a defect in the cranium.

27. A packaged calcium phosphate cement, said packaged cement comprising:
 a tubular element separated into first and second compartments by a removable barrier;
 dry reactants comprising a source of calcium and phosphate present in said first compartment that produce a flowable composition upon combination with a solution of a soluble silicate, wherein said flowable composition sets in an in vivo fluid environment in less than 20 minutes into a solid calcium phosphate containing product having a compressive strength of at least about 20 MPa upon reaction of said calcium and phosphate sources; and
 a solution of a soluble silicate present in said second compartment.

28. The packaged calcium phosphate cement according to claim 27, wherein said removable barrier is a clip.

29. The packaged calcium phosphate cement according to claim 27, wherein said removable barrier is a frangible barrier.

30. The packaged calcium phosphate cement according to claim 27, wherein said tubular element is present inside a second sterility maintaining element.

31. A method of producing a flowable composition that sets in an in vivo fluid environment into a said calcium phosphate containing product, said method comprising:
 combining:
  (a) a silicate solution containing a soluble silicate; and
  (b) dry reactants comprising a calcium source and a phosphate source, wherein said silicate solution and dry reactants are combined in a ratio sufficient to produce a flowable material that sets in an in vivo fluid environment in less than 20 minutes into a solid calcium phosphate containing product having a compressive strength of at least about 20 MPa upon reaction of at least said calcium and phosphate sources.

32. The method according to claim 31, wherein said ratio ranges from about 0.2:1 to 0.7:1.

33. The method according to claim 32, wherein said flowable composition is a paste.

34. The method according to claim 31, wherein said silicate solution is a solution of a soluble silicate having a concentration ranging from about 1% to 15%.

35. The method according to claim 31, wherein said flowable composition sets into said calcium phosphate containing product in a period of time ranging from about 5 to 10 minutes.

* * * * *